United States Patent [19]

Schneider et al.

[11] Patent Number: 5,656,608
[45] Date of Patent: Aug. 12, 1997

[54] AMINO ACID COMPOSITIONS AND METHODS OF TREATMENT USING SAME

[75] Inventors: Heinz Schneider, Cordast, Switzerland; Ronald G. Thurman, Chapel Hill, N.C.

[73] Assignee: Sandoz Nutrition Ltd., Berne, Switzerland

[21] Appl. No.: 392,694

[22] Filed: Feb. 23, 1995

[51] Int. Cl.$^6$ .............................. A01N 43/04; A61K 31/70
[52] U.S. Cl. .................... 514/42; 514/45; 514/49; 514/458; 514/474; 514/554; 514/663; 514/762
[58] Field of Search ........................... 514/42, 45, 49, 514/458, 474, 554, 663, 762

[56] References Cited

U.S. PATENT DOCUMENTS

| | | | |
|---|---|---|---|
| 4,414,202 | 11/1983 | Silvetti | 424/147 |
| 4,988,724 | 1/1991 | Ajani et al. | 514/399 |
| 4,994,442 | 2/1991 | Gil et al. | 514/45 |
| 4,994,492 | 2/1991 | Kendall et al. | 514/561 |
| 5,198,465 | 3/1993 | Dioguardi | 514/474 |
| 5,231,085 | 7/1993 | Alexander et al. | 514/44 |
| 5,430,064 | 7/1995 | Hirsch et al. | 514/554 |

FOREIGN PATENT DOCUMENTS

| | | |
|---|---|---|
| 2078712 | 3/1993 | Canada . |
| 0506965 | 10/1992 | European Pat. Off. . |
| 0614616 | 9/1994 | European Pat. Off. . |
| 2591893 | 6/1987 | France . |
| 9204023 | 3/1992 | WIPO . |
| 9305780 | 4/1993 | WIPO . |

OTHER PUBLICATIONS

Blum, et al., Life Sciences, vol. 14, pp. 557–565 (1974).
Jeevanandam, et al., The Lancet, pp. 1423–1426 (Jun. 30, 1984).
Derwent Abstract No. 93–183072/23 (1991).
Derwent Abstract No. 93–126956/16 (1991).
Derwent Abstract No. 89–286411/40 (1988).
Derwent Abstract No. 93–299541/38 (1984).
Butter, et al., Transplantation, vol. 56, pp. 817–822, No. 4, (Oct. 1993).
Weinberg, et al., American Journal of Physiology, vol. 258, pp. C1127–C1140, (1990).
Weinberg, et al., The Amer. Society for Clinical Investigation, Inc., pp. 1446–1454, vol. 80, (Nov. 1987).
Grimble, et al., J. Nutrition, vol. 122, pp. 2066–2073, (Jun., 22, 1992).
M. Schilling, et al., Transplantationsmedizin, vol. 6, pp. 140–143, (1994).
Ozaki, et al., Transplantations, vol. 58, No. 6, pp. 753–755 (1994).
Pathirana et al., Journal Nutrition, No. 7, pp. 1369–1375 (Jul. 1992).

*Primary Examiner*—Nathan M. Nutter
*Attorney, Agent, or Firm*—Carl W. Battle

[57] ABSTRACT

Composition comprising glycine and/or other amino acids are useful in treating or minimizing the effects of endotoxemia, hypoxia-reperfusion injury and infection.

14 Claims, No Drawings

AMINO ACID COMPOSITIONS AND METHODS OF TREATMENT USING SAME

The present invention relates to the use of glycine in minimizing the effects of endotoxemia, hypoxia-reperfusion injury and infection.

It is known that glycine prevents cell death induced by anoxia, oxidative stress and various toxic agents in a variety of cells. For example, glycine was reported to reduce cell damage caused by anoxia, potassium cyanide and t-butyl hydroxide. However, glycine was not found to protect suspended hepatocytes against injury caused by calcium ionophores or oxidative stress. Also, addition of glycine to liver graft storage solution did not improve survival in dogs.

It has now surprisingly been found that glycine is suitable for minimizing the effects of endotoxemia, hypoxia-reperfusion injury and infection and, accordingly, indicated for i.a. treatment and prophylaxis of endotoxic shock, sepsis, alcoholic liver disease (fibrosis, cirrhosis, alcoholic hepatitis, viral hepatitis and the like) and acute liver failure including pancreatic or intestinal disorders resulting therefrom such as inflammatory liver, chronic hepatitis, chronic pancreatitis, Crohn's disease and ulcer active colitis.

The favourable activity of glycine is indicated by tests:

Experiments indicate that glycine significantly reduces the release of TNF into the systemic circulation following endotoxic shock. It is known that TNF "primes" endothelial cells, i.e. induces production and display of Inter Cellular Adhesion Molecules (ICAM)—receptors mediating final interaction between activated neutrophils and endothelial cells. Said interaction induces infiltration of neutrophils into endothelium and severe damage in various organs resulting in MODS (Multi Organ Dysfunction Syndrome) and death.

Experiments also demonstrate the protective effect of glycine against liver injury by hypoxia-reoxygenation, showing i.a. that glycine at physiological concentrations of 240–300 mmol (in humans) provides more than half maximal protection in the rat liver reperfusion model. Test results with said reperfusion model indicate that glycine has cytoprotective effects and protects microcirculation.

The results indicate furthermore that glycine prevents or at least substantially suppresses ischemic/endotoxic liver and organ damage by suppressing the activation of Kupffer cells in the liver. It is well-known that activation of Kupffer cells results in production and release of a myriad of cytotoxic compounds, such as TNF, cytokines, reactive oxygen metabolites (radicals) and NO.

In comparison with the well-known fish oil induced partial protection against the effects of infection, test results indicate that the protective effect attained by administration of glycine is more profound and acute than that obtainable by fish oil treatment, whilst not impairing essential bodily processes. Glycine treatment is accordingly particularly indicated in trauma patients (polytrauma, burns, major surgery), patients with systemic inflammatory response syndrome (SIRS), septic patients, adult respiratory stress syndrome (ARDS) patients and patients with acute liver failure in whom no pretreatment is possible but an acute effect is desired.

It will be appreciated that glycine treatment is indicated to minimize the effect of infections. The infections may be wound infections, empyemas, bacteremias, abscesses, septicemias and the like. They may be caused by a variety of infectious agents, including bacteria, viruses, parasites, fungi and endotoxins. Glycine treatment and/or pretreatment is particularly indicated for patients at infection risk. High risk patients include patients having a lowered resistance due to immunosuppression.

Examples of high risk patients indicated for glycine treatment and/or pretreatment, are i.a. patients subject to radio- and/or chemotherapy, patients suffering from diabetes mellitus, from protein-malnourishment, gastrointestinal cancer surgery patients, cardiac surgery patients, patients subject to transplantations, patients having an increased risk of liver disease due to excessive alcohol consumption, patients suffering from human immunodeficiency virus-related infection and the like.

With respect to patients having an increased risk of liver disease due to excessive alcohol consumption, it has furthermore been established that glycine prevents liver injury due to chronic intragastric ethanol exposure in the rat. Further tests indicate that glycine prevents the transfer of alcohol from the stomach into the blood.

In view of the above-mentioned effects, there are provided pharmaceutical compositions, formulations and diets comprising glycine as well as methods of using glycine. For use in the compositions, formulations, diets and methods of the invention, glycine is conveniently employed in free amino acid form, in the form of glycine precursors, in particular alanine or serine, likewise in free amino acid form, in pharmacologically acceptable salt form of said amino acids, or in form of mixtures of said amino acids and/or pharmacologically acceptable salts thereof. Glycine is preferably used in free amino acid form, in pharmacologically acceptable salt form or in the form of a mixture of glycine in free amino acid form with glycine in pharmacologically acceptable salt form; most preferably glycine is in free amino acid form.

The term "amino acid of the invention" as used hereinafter is meant to refer to glycine, alanine and/or serine, in free amino acid form and/or pharmacologically acceptable salt form.

The invention therefore provides the use of amino acid of the invention in minimizing the effects of endotoxemia, hypoxia-reperfusion injury and infections; compositions containing an amino acid of the invention; the use of an amino acid of the invention in the manufacture of compositions for minimizing the effects of endotoxemia, hypoxia-reperfusion injury and infections; and a method of minimizing the effects of endotoxemia, hypoxia-reperfusion injury and infection comprising administering effective amounts of an amino acid of the invention.

The invention also provides a method of reducing the risk of death following endotoxic shock and/or hypoxia-reperfusion injury, in particular, in trauma (polytrauma, burn and post-operative patients as well as septic patients) comprising administering effective amounts of an amino acid of the invention.

The invention furthermore provides the use of an amino acid of the invention for treatment of patients having an increased risk of liver disease due to excessive alcohol consumption; the use of an amino acid of the invention in the manufacture of compositions for treatment of patients having an increased risk of liver disease due to excessive alcohol consumption and a method of treating patients having an increased risk of liver disease due to excessive alcohol consumption comprising administering effective amounts of an amino acid of the invention.

The invention also provides the use of an amino acid of the invention as additive to foods, soft drinks, vitamins or pharmaceutical preparations for treatment of ethanol toxicity and a method of preventing ethanol toxicity employing an effective amount of an amino acid of the invention.

For use according to the invention, an amino acid of the invention may be administered enterally or parenterally. It will be appreciated that, for acute treatment, the parenteral application route is preferred. The parenteral application route is, for example, also indicated where the objective is to control the effects of chronic endotoxemia. Subsequent or prophylactic treatment is conveniently enterally, e.g. orally or by tube feeding, insofar the patient's condition allows enteral feeding.

Typical compositions of an amino acid of the invention suitable for use according to the invention and provided by the invention, include the following:

Aqueous solutions consisting essentially of 0.1% to 90% by weight of an amino acid of the invention, the rest being water (hereinafter solution of the invention).

The solution of the invention may be in concentrated form, comprising 15 to 90%, preferably 40 to 60% by weight of an amino acid of the invention or in application form comprising 0.1 to 15%, e.g. 0.1 to 5% by weight of an amino acid of the invention. Concentrated forms are suitable for dilution to application forms or for acute treatment.

Application forms having a lower content (e.g. 0.1 to 5%) of amino acid of the invention, will in general be indicated for prophylaxes purposes; application forms having a higher content (e.g. 5% to 40% by weight) of amino acid of the invention will in general be more suitable for acute treatment.

Other formulations suitable for use in the method of the invention in particular for parenteral application include infusion fluids such as Ringer's injection, lactated Ringer's injection, crystalloids, colloids or other plasma substitutes, in association or enriched with 0.1 to 5.0 g amino acid of the invention per liter infusion fluid.

The use of such infusion fluids enriched with an amino acid of the invention is particularly appropriate where fluid therapy of patients in need of treatment with an amino acid of the invention is indicated. This is for example the case where acute treatment is required and hypovolaemia is a symptom.

Ringer's Injection is a sterile solution, containing from 3.23 to 3.54 g of sodium (equivalent to from 8.2 to 9.0 g of sodium chloride), from 0.149 to 0.165 of potassium (equivalent to from 0.285 to 0.315 g of potassium chloride), from 0.082 to 0.098 g of calcium (equivalent to from 0.3 to 0.36 g of calcium chloride, in the form of $CaCl_2 \cdot 2H_2O$), from 5.23 to 5.80 g of chloride (as NaCl, KCl and $CaCl_2.2H_2O$) and water in sufficient quantity to give 1000 ml solution.

Lactated Ringer's Injection is a sterile solution known to contain from 2.85 g to 3.15 g sodium, as chloride and lactate), from 0.141 to 0.173 g of potassium (equivalent to from 0.27 g to 0.33 g of potassium chloride), from 0.049 to 0.060 g calcium (equivalent to from 0.18 g to 0.22 g of $CaCl_2.2H_2O$), from 2.31 g to 2.61 g of lactate, from 3.68 to 4.08 g of chloride (as NaCl, KCl and $CaCl_2.2H_2O$) and water in sufficient quantity to give 1000 ml solution.

The terms crystalloids and colloids in connection with fluid therapy are known in the art. They include plasma substitutes such as Haemaccel (polygeline based) and Gelofusine (gelatin based).

Where the purpose of the treatment is to prevent or minimize the effects of endotoxemia, hypoxia-reperfusion injury or infection it is indicated to use an amino acid of the invention in combination with one or more of the following components:

(i) omega-3 polyunsaturated fatty acids (PUFAs) where desired in admixture with omega-6 PUFAs;

(ii) arginine or other pharmacologically acceptable compounds associated with the synthesis of polyamines; and (iii) RNA or one or more nucleotides, nucleosides, or nucleobases or mixtures thereof.

Accordingly, the invention provides compositions comprising:

(a) an amino acid of the invention in association with one or more components selected from (b) omega-3 PUFAs;

(c) arginine or other pharmacologically acceptable compounds associated with the synthesis of polyamines;

(d) RNA effective in minimizing the effects of endotoxemia, hypoxia-reperfusion injury and infection (hereinafter diets of the inventions).

In general, favourable effects are obtained when administering the latter diets of the invention in the form of a formula diet, which may, depending on the circumstances be a complete formula diet (i.e. a diet supplying essentially all required energy, amino acids, vitamins, minerals and trace elements). or a diet supplement. The diet will conveniently be taken in liquid form.

The daily amount of glycine to be administered to give the desired effect (minimizing the effects of endotoxemia, hypoxia-reperfusion injury and infections and/or minimizing the risk of liver disease due to excessive alcohol consumption) will, in general, lie in the range of 1.5 g to 80 g amino acid of the invention. Such daily amounts of amino acid of the invention are suitable for treatment of the desired effects as well as for prophylactic/pretreatment.

Where compositions of an amino acid of the invention in combination with one or more of the above-mentioned components (b), (c) and (d) are used, such compositions will conveniently comprise in one daily dose (a) from 1.5 g to 80 g of an amino acid of the invention in association with at least one of (b) 0.1 g to 20 g of omega-3 PUFAs;

(c) 3 g to 40 g of arginine or an equivalent amount of one or more other pharmacologically acceptable compounds associated with the synthesis of polyamines, or an equivalent amount of a mixture of arginine with such compounds; and (d) 0.1 g to 4.0 g of RNA or an equivalent amount of one or more nucleotides, nucleosides or nucleobases or mixtures thereof.

Omega-3 PUFAs are conveniently protected against peroxidation.

Pharmacologically acceptable ways of protecting omega-3 PUFAs against peroxidation are known in the art. They include pharmacologically acceptable micro-encapsulation of omega-3 PUFAs and the use of pharmacologically acceptable antioxidants.

A typical example suitable for use as pharmacologically acceptable micro-encapsulation agents is starch. The micro-encapsulation can be effected in a manner known per se. The micro-encapsules may be coated in a manner known per se, by pharmacologically acceptable coating agents such as Gum Arabic.

Typical examples of antioxidants suitable for use in the method of the invention include antioxidant vitamins such as Vitamin C, Vitamin E or mixtures thereof.

The amount of antioxydant added should be sufficient to prevent peroxidation of the omega-3 PUFAs. Such amounts can be easily calculated. In general, for convenience, any antioxydants employed to prevent peroxidation, will be employed in excess. It will be appreciated that the presence of any other agent administered in association with the omega-3 PUFAs may require adjustment of the amount of antioxidant to be employed.

The omega-3 PUFAs may be employed in free acid form, in a form suitable for the physiological supply of omega-3 PUFAs, e.g. in triglyceride form, or in the form of pharmacologically acceptable natural sources of omega-3 PUFAs. Such natural sources include linseed oil and fish oils such as menhaden oil, salmon oil, mackeral oil, tuna oil, codliver oil and anchovy oil. Said natural sources, in particular, the fish oils, comprise substantial amounts of omega-6 fatty acids. Where the omega-3 PUFAs are employed in triglyceride form, said triglycerides may comprise esters with other pharmacologically acceptable fatty acids.

Preferred omega-3 PUFAs include eicosapentaenoic acid (EPA) and docosahexaenoic acid (DHA), in free acid form, in triglyceride form or in form of natural sources having a high EPA and/or DHA content.

The daily amount of omega-3 PUFAs to be administered will conveniently lie in the range of from 2 g to 5 g.

It will be appreciated that omega-3 PUFAs may be administered in higher amounts than those indicated hereinabove, and that such higher amounts will in general not impair the desired effect or provoke undesired side effects.

Compounds particularly suitable for use as component (c) in the formulation of the invention include L-arginine and L-ornithine in free form, pharmacologically acceptable salt form, e.g. in the form of a salt with phosphoric acid, citric acid, tartaric acid, fumaric acid, adipic acid or lactic acid, or in small peptide form.

The term small peptides as used herein refers to peptides having from 2 to 6, preferably from 2 to 4 amino acids.

Component (c) will conveniently be administered in a daily amount supplying from 7.5 to 20 g L-arginine or L-ornithine.

Component (d), if administered in association with an amino acid of the invention will conveniently be administered in a daily amount of from 1.7 to 2.0 g.

As already indicated, omega-3 PUFAs will conveniently be administered in the form of fish oils, protected or not against peroxidation. Such fish oils also comprises omega-6 PUFAs.

Omega-6 PUFAs have also a favourable effect on the immune response and on the resistance to infection upon surgery. Accordingly, diets of the invention will conveniently comprise omega-6 PUFAs.

For the purpose of the invention the omega-6 PUFAs may be in free acid form or in a form suitable for the physiological supply of omega-6 PUFAs, e.g. in triglyceride form. Examples of omega-6 PUFAs particularly appropriate for use according to the invention, include linoleic acid and arachidonic acid, linoleic acid being most preferred. Examples of suitable omega-6 PUFA sources are known in the art. They include fish oils and vegetable oils. Examples of omega-6 PUFA sources having a high linoleic acid content such as safflower oil, sunflower oil, soya oil, cotton oil and corn oil.

Administration of a daily amount of omega-6 PUFAs in the range of from 1.5 to 5.0 g will in general suffice to attain a favourable effect.

In addition to components (b), (c) and (d), and omega-6 PUFAs further components may be added to the diets of the invention and may have a beneficial effect on the activity of the amino acid of the invention. An example of such beneficial components are omega-9 PUFAs. A preferred natural source for such fatty acid mixtures are fish oils. For taste and other reasons, the fish oils will, in oral application forms, preferably be used in encapsulated form.

The compositions of the invention may be formulated in a form suitable for parenteral or enteral administration. They are particularly appropriate for enteral use, e.g. for oral administration, nasal administration and/or tube feeding. Such compositions are conveniently administered in the form of an aqueous liquid. The formula diets of the invention suitable for enteral application are accordingly preferably in aqueous form or in powder form, whereby the powder is conveniently added to water prior to use. For use as tube feeding, the amount of water to be added will i.a. depend on the patient's fluid requirements and condition.

The formula diets of the invention may comprise vitamins, mineral, trace elements as well as additional nitrogen, carbohydrate and fatty acid sources.

They comprise conveniently also nutritionally acceptable fibre, preferably soluble fibre. The term soluble fibre as used herein refers to fibers which are able to substantially undergo fermentation in the colon to produce short chain fatty acids. Examples of suitable soluble fibers include pectin, guar gum, locust bean gum, xanthan gum. They may be hydrolysed or not. For adults the total amount of soluble fibre per day will conveniently lie in the range of from 3 to 30 g/day.

Where the formula diet of the invention is intended for use as a supplement (e.g. pre-operative treatment), the amount of energy supplied by it should not be too excessive, in order not to unnecessarily suppress the patients appetite. The supplement should conveniently comprise energy sources in an amount supplying from 600 to 1000 Kcal/day. For use as a complete formula diet (e.g. for post-operative treatment, treatment of trauma), the diets of the invention will conveniently supply from 600 to 1500 Kcal/day. The contribution of the nitrogen source, carbohydrate source and lipid source to the total daily caloric may vary within wide ranges. In preferred compositions of the invention the carbohydrate source provides for 40 to 70% of the total energy supply and, the nitrogen and fatty acid source each for 15 to 30% of the total energy supply of the composition. For use as complete diet, the diet of the invention will conveniently be administered in liquid form in volumes in the range of from 500 ml to 3000 ml. For use as a supplement, the administration may be in powder or liquid form.

Examples of suitable nitrogen sources include nutritionally acceptable proteins such as caseinates, whey and/or protein hydrolysates.

Examples of suitable carbohydrate sources include maltodextrins.

Examples of suitable fatty acid energy supply sources include triglyceride sources.

Examples of vitamins suitable for incorporation in the composition of the invention include vitamin A, vitamin D, vitamin E, vitamin K, vitamin C, folic acid, thiamin, riboflavin, vitamin $B_6$, vitamin $B_{12}$, niacin, biotin and panthotenic acid in pharmaceutically acceptable form.

Examples of mineral elements and trace elements suitable for incorporation in the composition of the invention include sodium, potassium, calcium, phosphorous, magnesium, manganese, copper, zinc, iron, selenium, chromium and molybdenum in pharmaceutically acceptable form.

In particular, the compositions of the invention will preferably comprise beta-carotene (vitamin A), vitamin E, vitamin C, thiamine, vitamin $B_{12}$, choline, selenium and zinc in pharmaceutically acceptable form.

The diets of the invention are i.a. indicated for minimizing the effects of endotoxemia, hypoxia-reperfusion injury and infection in patients in need of such treatment.

Typical patients, indicated for treatment with diets of the invention, include patients before and following major operative procedures, i.e. any operative procedure requiring general anesthesia such as cardiac bypass surgery and major upper gastrointestinal surgery.

It follows from the surprising pharmacological activity of glycine in minimizing the effects of endotoxemia, hypoxia-reperfusion injury and infection that amino acids of the invention and especially the diets of the invention are particularly suitable for treatment of patients due for surgery. Such pretreatment will be most effective when administering the diet of the invention in the form of a supplement. The supplement will advantageously be administered over a period of 3 days or longer. In general, a pretreatment starting 3 to 6 days before surgery, and during said 3–6 day period will be sufficient to attain the desired effect. For pretreatment or prophylactic purposes administration of a supplement containing from 1.5 g to 80 g amino acid of the invention in association with from 2 to 5 g Component (b) (omega-3-PUFAs) and/or with Component (c) supplying from 7.5 to 20 g L-arginine or L-ornithine per day, will in general give the desired effect.

The supplement will conveniently be administered in the form of unit doses suitable for administration of the supplement 3 to 4 times per day. Where the diets of the invention comprise energy sources, it is appropriate not to supply more than 1500 Kcal/day.

Where acute treatment of patients following excessive ethanol exposure is necessary, the amino acid of the invention will conveniently be administered parenterally. Typical administration forms suitable for such acute treatment are e.g. the aqueous solutions disclosed hereinabove.

Where it is desired to minimize alcohol uptake into the blood by glycine induced alcohol elimination in the stomach, the amino acid of the invention will conveniently be provided in a conventional oral administration form, such as granules, tablets, capsules, liquids (including soups and drinks such as soft drinks, thirst quenchers), powders, formula diets etc. When formulated in a pharmacologically acceptable formulation form such as a capsule or tablet form, such compositions will conveniently contain 0.2 to 90% by weight, preferably from 30 to 50% by weight of an amino acid of the invention. In general, satisfactory alcohol (ethanol) elimination from the stomach is obtained when administering a total amount within the range of from 0.01 to 5.0 g of one or more of the amino acids selected from the group consisting of glycine, alanine and serine, in free form and/or pharmacologically acceptable salt form per kg body weight. The administration is conveniently orally, and prior to alcohol intake.

Typical pharmacologically acceptable formulation forms for oral administration will further comprise pharmacologically acceptable diluents, carriers, vitamins, spices, pigments and/or other adjuvants well known to the skilled person to be suitable for incorporation into such formulation.

Where desired, the amino acid of the invention may also be used in association with L-aspartate and/or L-asparagine.

The diets and formulations of the invention may be obtained in a manner known per se, e.g. by admixing the ingredients.

The following examples illustrate the invention:

EXAMPLE 1

Effects of Glycine on Reperfusion Injury In A Low-flow, Reflow Liver Perfusion Mode 1.1 Summary Livers are perfused at low flow rates around 1 ml g/min for 75 min. which causes cells in the pericentral regions of the liver lobule to become anoxic due to insufficient delivery of oxygen. When normal flow rates (about 4 ml/g/min) are restored for 40 min. an oxygen-dependent-reperfusion injury occurs. Upon reflow, lactate dehydrogenase (LDH), a cytosolic enzyme, and malondialdehyde (MDA), an end product of lipid peroxidation, are released into the effluent perfusate. LDH increases from basal levels of about 1 to 35 IU/g/h in livers from control rats. Glycine (0.06–2 mM) minimizes enzyme release in a dose-dependent manner (half-maximal decrease=180 µM), with maximal values reaching only 5 IU/g/h with 2 mM glycine. Reflow for 40 minutes following 75 minutes of low-flow hypoxia causes death in about 30% of previously anoxic parenchymal cells in pericentral regions; however, infusion of glycine (2 mM) decreases cell death to less than 10%. Bile is released at rates around 42 ul/g/h in livers from control rats, which rate is not significantly altered by glycine. MDA production during reperfusion tends to decrease with glycine, changes are not statistically significant. Trypan blue distribution time, an indicator of hepatic microcirculation is reduced significantly at 5 and 40 minutes after reflow, but changes are about 2-fold greater at later than earlier time points (half maximal decrease=180 µM). Taken together, these data indicate that a reperfusion injury, which occurs in previously hypoxic pericentral regions of the liver upon reintroduction of oxygen, is minimized by glycine.

1.2 Methods

Animals used: Male Sprague-Dawley rats weighing between 180–210 g and fed a Purina diet. Rats were fasted for 24 h prior to surgery.

Liver Perfusion: Rats were anesthetized with pentobarbital sodium (50 mg) before surgery and livers were removed surgically and perfused via a cannula inserted into the portal vein with Krebs-Henseleit bicarbonate buffer (pH 7.4, 37° C.) saturated with an oxygen-carbon dioxide (95:5) mixture in a non-recirculating system (Krebs-Henseleit, 1932). After surgery, livers were perfused at flow rates around 1 ml/g/min for 75 minutes (low-flow). Subsequently, livers were perfused at normal flow rates (4 ml/g/min) for 40 minutes (reflow). Glycine was dissolved in Krebs-Henseleit biocarbonate buffer (pH 7.4, 37° C.) and infused into the liver continuously beginning 10 minutes before reflow at rates resulting in final concentrations ranging from 0.06–2 mM.

Lactate dehydrogenase (LDH): LDH activity in the perfusate was determined using standard enzymatic techniques (Bergmeyer, 1988). Three ml of perfusate were mixed thoroughly with a reagent containing 15% trichloroacetic acid, 0.375% thiobarbituric acid and 0.25N hydrochloric acid and heated for 15 minutes in a boiling water bath. After cooling, samples were centrifuged at 1000×g for 10 minutes and the absorbance of the supernatant was determined at 535 nm. Rates of release of LDH expressed per gram wet weight of liver per hour.

Trypan Blue Distribution Time and Histological Procedures: To assess microcirculation and cell death in the liver, trypan blue was infused into the liver at the end of all experiments at final concentrations of 0.2 mM (Belinsky et al., 1984). The time for the liver surface to turn evenly dark blue was recorded. Excess dye was removed by perfusion with Krebs-Henseleit buffer for an additional 10 minutes. Subsequently, livers were perfused with 1% paraformaldehyde for 10 minutes and fixed tissue was embedded in paraffin and processed for light microscopy. Sections were stained only with eosin, a cytoplasmic stain, so that trypan blue could be identified readily in the nuclei of damaged cells.

All nuclei of parenchymal cells in a zone radiating five cells from either periportal or pericentral regions were identified as trypan blue-positive or negative. The percentage of staining was calculated from the number of stained nuclei divided by the total number of cells in any given region.

Statistical Analysis: Student's-t-test or ANOVA was used where appropriate. Differences were considered significant when the p-value was less than 0.05.

1.3 Results

Effects of Glycine on 1Hepatocellular Damage in a Low-flow, Re-flow Perfusion

Model: During the low-flow period, LDH release was minimal (around 1 IU/g/h at 75 minutes). When the flow rate was increased to 4 ml/g/min, however, LDH release increased gradually, reaching a new steady-state value in about 30 minutes. Maximal LDH release during the reperfusion period was around 35 IU/g/h in controls, but was reduced significantly by glycine treatment in a dose-dependent manner. When the concentration of glycine was increased to 2 mM, LDH release was reduced to around 5 IU/g/h; half-maximal decreases occurred with 180 µM glycine.

Trypan blue uptake indicates irreversible loss of cell viability in the liver lobule. Reflow for 40 minutes following 75 minutes of low-flow hypoxia caused death in about 30% of parenchymal cells in pericentral regions, but only affected about 2% of cells in previously normoxic periportal regions. Infusion of glycine (2 mM) decreased cell death in pericentral areas to 9%. Taken together, reperfusion injury, which occurs when oxygen is reintroduced into previously anoxic pericentral regions of the liver lobules, was clearly minimized by acute glycine infusion in a dose-dependent manner.

Effects of Glycine on Trypan Blue Distribution: Trypan blue distribution time, an indicator of the hepatic microcirculation, was slightly but significantly lower in glycine-infused livers than in controls (about 190 seconds in glycine-treated liver and 225 seconds in controls, respectively, p<0.05, n=5) when trypan blue was infused into the liver 5 minutes after reperfusion. However, values were reduced dramatically by glycine in a dose-dependent manner when trypan blue was infused at the end of 40 minutes of reperfusion. It took about 460 seconds for trypan blue to distribute evenly in controls, whereas values were reduced to about 250 seconds when 2 mM glycine was infused. The concentration which caused half-maximal decrease in trypan blue distribution time was also around 180 µM.

1.4 Conclusions

Glycine minimized LDH release and cell death almost completely during reperfusion in a dose-dependent manner. Glycine has accordingly potent cytoprotective effects against reperfusion injury in a low-flow, reflow liver perfusion model in the rat.

Trypan blue distribution time was reduced by glycine in a dose-dependent manner, with the half-maximal effect similar to the cytoprotective effect of glycine (0.18 mM). Since trypan blue distribution time can be influenced not only by disturbances of the hepatic microcirculation but also by hepatic cell injury, trypan blue distribution time was measured after only 5 minutes of reflow, when reperfusion injury was minimal. This value was also reduced significantly by glycine but to a smaller extent, indicative of improved hepatic microcirculation.

Other possible mechanisms related to anoxia and reperfusion injury such as ATP depletion and alteration of mitochondrial function were also investigated. Bile production, a highly energy-dependent process, was not affected by glycine, indicating that glycine did not minimize ATP depletion, and oxygen uptake, an indicator of mitochondrial function, was not altered by glycine either, making these possibilities unlikely.

In conclusion, glycine improves hepatic microcirculation and protects against oxygen-dependent reperfusion injury. This effect may be related to actions on sensitive cell types other than parenchymal cells in the liver, such as endothelial or Kupffer cells.

EXAMPLE 2

Effects Of Dietary Glycine On Survival and Liver Injury In The Rat 2.1 Experiment Male Sprague-Dawley rats (200–250 g) were fed, ad libitum, by powder diet containing 20% by weight of casein (control diet) or 5% by weight of glycine and 15% by weight of casein (glycine diet) resp. for 3 days prior to the experiments.

The rats were then injected lipopolysaccharide (LPS; 10, 20 and 30 mg/kg resp.) from the tail vein and mortality was assessed 24 hours after the injection. If the rats survive 24 hours, they are considered safe as no late mortality is observed.

2.2 Observations a) The 5% glycine diet offers a 100% protection against an LPS dose of 10 mg/kg compared to 50% mortality in the control group significant at the p<0.05 level. At an LPS dose of 20 mg/kg a 30% mortality was observed with 5% glycine diet and a 70% mortality with the control diet. At 30 mg/kg LPS mortality increased to 90% in the glycine treated animals and to 100% in the controls.

b) From the survivors, the liver enzyme AST (Aspartate Aminotransferase; a transaminase) was measured as indication for liver damage. The AST level was markedly and significantly reduced in the glycine fed rats (from 2000 IU/L in untreated fed rats treated with an LPS dose of 10 mg/kg).

c) In a parallel experimental series, the effect of glycine diet on tumour necrosis factor (TNF) was assessed. Serum TNF was measured by ELISA. After injection of 10 mg/kg LPS, serum TNF increased rapidly in rats fed with the control diet to values over 6000 pg/ml, 60 min after injection, before declining to control values. This increase was significantly suppressed (by at least 50%; p<0.05) in rats fed with the 5% glycine diet, whereby the peak was attained 150 min after injection.

d) Liver and lung specimens for histology were taken 24 hr after injection of LPS (10 mg/kg) and hematoxylin-eosin stained.

Rats fed with the control diet showed many necrotic area and neutrophil infiltration in the liver and marked interstitial edema with neutrophil infiltration in the lung. Rats fed with glycine diet showed less necrosis in the liver and less pulmonary edema than rats fed with the control diet.

e) Serum glycine concentration was determined by HPLS from 2 groups of rats fed with control diet and glycine diet resp., and of which each group had been given a LPS injection (10 mg/kg i.v. in the tail vein).

A rat fed with glycine diet without LPS treatment showed remarkably higher glycine concentration (1892

μM/l) than rats fed with control diet (150 μM/l) and without LPS injection. The rats fed with glycine diet maintained the high concentration of glycine (1727±515 μM/l) 6 hr after LPS injection; the rats fed with control diet had 6 hr after the LPS injection a serum glycine concentration of 278±μM/l.

EXAMPLE 3

Effect Of Pre-treatment With Glycine On The Mortality After Partial Hepatic Ischemia/Reperfusion And LPS Injection After 3 days feeding with control diet and glycine diet resp., rats were given partial hepatic ischemia for 90 min. under methoxyflurane anesthesia. A sublethal dose of LPS (5 mg/kg) was injected via tail vein 6 hr after reperfusion.

All of the control rats without LPS injection survived for 24 hours after 90 min. partial hepatic ischemia/reperfusion (n=4).

All rats fed with control diet and with 90 min. partial hepatic ischemia/reperfusion died within 24 hr after the (sublethal) LPS injection (n=4).

Pretreatment of rats with glycine diet markedly improved the survival (5 rats out of 6 survived) under the same conditions (90 min. partial hepatic ischemia/reperfusion and given the LPS injection) during the observation period (24 hours from the injection time); $p<0.05$ with Fisher's test).

EXAMPLE 4

Effects Of Dietary Glycine On Alcohol-Induced Liver Injury

4.1 Materials and Methods a. Animals

In Male Wistar rats, weighing 300 to 320 mg each, intragastric cannulas were inserted as described by Tsukamoto and French. Cannulas were tunnelled subcutaneously to the dorsal aspect of the neck and attached to infusion pumps by means of a spring-tether device and swivel allowing complete mobility of rats in metabolic cages. Animals were infused continuously with a high-fat liquid diet containing ethanol for up to 4 weeks. All animals received humane care in compliance with institutional guidelines.

b. Diet

A liquid diet described by Thompson and Reitz was used. It contained corn oil as fat (37% of total calories), protein (23%), carbohydrate (5%), minerals and vitamins, plus ethanol or isocaloric maltose-dextrin (35%), hereinafter designated liquid control diet. Glycine (2 or 5% by weight) was added to the liquid control diet; such diets are hereinafter referred to as liquid 2% glycine diet and liquid 5% glycine diet resp.

c. Urine Collection and Assay of Ethanol

Concentration of ethanol in urine, which are representative of blood alcohol levels were measured daily. Rats were housed in metabolic cages that separated urine from feces, and urine was collected over 24 hours in bottles containing mineral oil to prevent evaporation. Each day at 0900 h, urine collection bottles were changed and an 1-ml sample was stored at −20° C. in a microtube for later ethanol analysis. Ethanol concentration was determined by measuring absorbance at 360 nm resulting from the reduction of $NAD^+$ to NADH by alcohol dehydrogenase.

d. Blood Collection and Asparate Aminotransferase (AST)

Blood was collected via the tail vein once a week and centrifuged. Serum was stored at −20° C. in a microtube until assayed for AST by standard enzymatic procedures. Whole blood (100 μl) was also assayed for ethanol as described below, and hepatic portal blood was also collected when the liver biopsy were performed at the 2nd and 4th week of treatment with ethanol.

e. Ethanol Assay in Breath, Peripheral and Portal Blood, Feces and Stomach Contents To determine concentrations of ethanol in breath, rats were forced to breathe into a closed heated chamber (37° C.) for 20 sec. and 1 ml of breath was collected with a gas-tight syringe. Ethanol concentrations were analysed by gas chromatography (GC). Ethanol in peripheral and portal blood was also assayed by GC. Blood (100 μl) was mixed with 900 μl of distilled water in a closed flask incubated for 30 min. at 37° C., and 1 ml of the gas phase was collected and assayed by GC. Rat feces were collected directly from the anus, homogenized in distilled water and incubated and analysed as described above for blood. Stomach contents were also collected when rats were sacrificed at the 4th week of ethanol treatment, and analysed as described for blood.

f. Measurement of Glycine Concentration in Blood

After 4 weeks of ethanol treatment, 500 μl of plasma was collected and stored at −80° C. for determination of glycine concentration in blood by HPLC. Quantitative analysis of glycine in heparinized plasma was carried out using the PICP-TAG (Waters, Milford, Mass.) method. Plasma samples were first hydrolysed with HCl, and then derivatized with phenylisothiocyanate (PITC) to produce phenylthiocarbamyl (PTC) amino acids. Amino acids including glycine were determined by automated gradient reserve phase high-pressure liquid chromatography (HPLC).

g. Pathological Evaluation

Rats underwent liver biopsy and autopsy after 2 and 4 weeks of treatment with ethanol. Livers were formalin-fixed, embedded in paraffin and stained with hematoxylin and eosin to assess steatosis, inflammation and necrosis. Liver pathology was scored as described by Nanji et al. as follows: steatosis (the percent liver cells containing fat): <25%=1+; <50%=2+; <75%=3+, >75%=4+; inflammation and necrosis: 1 focus per low-power field=1+; 2 or more=2+.

h. Statistics

ANOVA or Student's t-test was used for determination of statistical significance as appropriate. For comparison of pathological scores, the Kruskal-Wallis ANOVA for ranks was used. A p value less than 0.05 was selected before the study as the level of significance.

4.2 Results

Body weights of rats fed with the liquid control diet, the liquid/glycine diet and the liquid 5% glycine diet, during the course of this study had a tendency to decline during the first week was observed. The body weights then stabilized and were constant during the following 3 weeks of treatment with ethanol. There were no significant differences in body weight among the groups studied.

Ethanol intake was gradually increased to 9 to 10 gm/kg/day during the first week after surgery. Intake was between 10 and 13 gm/kg/day during weeks 2–4, and there were no significant differences between the groups. Glycine concentration in plasma after 4 weeks of treatment was 779±66 μmol/L in rats receiving the liquid 5% glycine-containing diet, and was 198±16 μmol/L in ethanol fed rats.

Representative plots of daily urine alcohol concentrations in rats fed with the liquid control diet and the liquid glycine diets were determined. Alcohol levels fluctuate in a cyclic pattern from near zero to greater than 300 mg/dl in rats fed with the liquid control diet, even though ethanol was infused continuously. In rats fed with one of the liquid glycine diets, alcohol concentrations were very low but were still cyclic. Mean urine alcohol concentrations were reduced significantly in a dose-dependent manner; a 50% reduction of the mean urine alcohol concentration was obtained by feeding with the liquid 2% glycine diet, a 70% reduction with the liquid 5% glycine diet.

Serum AST in rats fed with the liquid control diet increased gradually with time of exposure and reached a level of 183 IU/L after 4 weeks (control value 70 IU/L). This increase was attenuated significantly by both glycine treatments at every point during the study. After 4 weeks of treatment, serum AST level was 66 IU/L in 2% glycine-treated rats fed with the liquid 2% glycine diet and was 100' IU/L in the group fed with the liquid 5% glycine diet.

In rats fed with the liquid control diet, slight steatosis was observed after only 2 weeks of treatment. After 4 weeks of treatment with said liquid control diet, obvious fatty changes were not apparent in control rats, not treated with ethanol. In rats fed with liquid 2% glycine and liquid 5% glycine diet, fatty changes were attenuated and necrosis and inflammation were almost totally absent. The reductions of steatosis and necrosis were statistically significantly after feeding with the liquid glycine diets; only a tendency for reduction of inflammation was observed after feeding with the liquid glycine diets because of variability.

Eventually, alcohol in stomach contents in glycine-treated rats was also reduced dramatically. Therefore, it is clear that glycine reduces the ethanol concentration in the stomach, possibly by effects on ethanol metabolism.

4. The method of claim 3 wherein said solution comprises from 0.1 to 90% by weight of one or more amino acids selected from the group consisting of glycine, alanine and serine or mixtures thereof, wherein said amino acids are in free form or pharmacologically acceptable salts.

5. The method of claims 3 or 4, wherein said solution is an infusion fluid enriched with one or more amino acids selected from the group consisting of glycine, alanine and serine or mixtures thereof, wherein said amino acids are in free form or pharmacologically acceptable salts.

6. The method of claim 5 wherein said infusion fluid contains per liter of infusion fluid from 0.1 to 5.0 g of one or more amino acids selected from the group consisting of glycine, alanine and serine or mixtures thereof, wherein said amino acids are in free form or pharmacologically acceptable salts.

7. The method of claims 1 or 2, comprising administering:
(a) one or more of said amino acids selected from the group consisting of glycine, alanine and serine, or mixtures thereof in free form or pharmacologically acceptable salt form;
in combination with
(b) omega-3 polyunsaturated fatty acids;
(c) arginine, ornithine, or pharmacologically acceptable salts of arginine or ornithine; or
(d) RNA, nucleotide or, nucleoside;
or mixtures of one or more of b), c) or d).

8. The method of claim 7 comprising administering daily amounts of
(a) 1.8 to 80 g of one or more of said amino acids selected from the group consisting of glycine, alanine and serine or mixtures thereof, in free form or pharmacologically acceptable salts
in combination with
(b) 2 to 5 g omega-3 polyunsaturated fatty acids;

TABLE 1

Effect of Glycine on ethanol concentrations in rats on the Tsukamoto-French Model

| Treatment | Breath | Feces | Urine A.M. | Urine 24 hr | Blood Tail | Stomach Portal Vein | |
|---|---|---|---|---|---|---|---|
| Ethanol | 108 ± 12 | 82 ± 21 | 184 ± 12 | 211 ± 16 | 199 ± 45 | 357 ± 65 | 761 ± 625 |
| Ethanol + 5% Glycine | 5 ± 4*** | 15 ± 11* | 26 ± 25** | 24 ± 8*** | 21 ± 13** | 10 ± 7*** | 26 ± 41* |

Breath, feces, blood and stomach contents were collected from rats and analysed by headspace gas chromatography. Urine samples were analysed enzymatically. Samples are taken from a total of 6 rats. Results are expressed as Mean ± S.E.M.
*p < 0.05;
**p < 0.01;
***p < 0.001 for comparisons of ethanol vs. ethanol + glycine-fed rats values by Student's t-test.

We claim:
1. A method for treatment of endotoxemia which comprises administering enterally or parenterally to a patient in need of such treatment a physiologically effective amount of one or more amino acids selected from the group consisting of glycine, alanine and serine or mixtures thereof, wherein said amino acids are in free form or pharmacologically acceptable salts.

2. A method of reducing risk of death of patients following an endotoxic shock or hypoxia-reperfusion injury comprising administering enterally or parenterally to patients in need of such treatment an effective amount of one or more amino acids selected from the group consisting of glycine, alanine and serine or mixtures thereof, wherein said amino acids are in free form or pharmacologically acceptable salts.

3. The method of claims 1 or 2 wherein said amino acid is administered in aqueous solution form.

(c) 7.5 to 20 g L-arginine or L-ornithine; or
(d) 1.7 to 2.0 g RNA;
or mixtures of one or more of b), c) or d).

9. The method of claim 1 wherein said amino acids, salts and mixtures thereof are administered in the form of a formula diet.

10. The method of claim 9 which comprises using a formula diet containing energy sources in an amount supplying from 600 to 1500 Kcal/day.

11. The method of claim 10 wherein said formula diet is administered in aqueous liquid form supplying from 500 to 3000 ml water per day.

12. The method of claim 7 wherein said omega-3 polyunsaturated fatty acids are encapsulated for protection against peroxidation.

13. The method of claim 7 wherein said omega-3 polyunsaturated fatty acids are protected against peroxidation using Vitamin C, Vitamin E or a mixture thereof.

14. The method of claim 7 wherein said omega-3 polyunsaturated fatty acids are in the form of fish oil.

* * * * *

REEXAMINATION CERTIFICATE (4160th)

United States Patent [19]
Schneider et al.

[11] B1 5,656,608
[45] Certificate Issued Sep. 26, 2000

[54] AMINO ACID COMPOSITIONS AND METHODS OF TREATMENT USING SAME

[75] Inventors: Heinz Schneider, Cordast, Switzerland; Ronald G. Thurman, Chapel Hill, N.C.

[73] Assignee: Novartis Nutrition Ltd., Berne, Switzerland

Reexamination Request:
No. 90/005,529, Oct. 12, 1999

Reexamination Certificate for:
Patent No.: 5,656,608
Issued: Aug. 12, 1997
Appl. No.: 08/392,694
Filed: Feb. 23, 1995

[51] Int. Cl.[7] ............... A01N 43/04; A61K 31/70
[52] U.S. Cl. ............... 514/42; 514/45; 514/49; 514/458; 514/474; 514/554; 514/663; 514/762
[58] Field of Search ............... 514/42, 45, 49, 514/458, 474, 554, 663, 762

[56] References Cited

FOREIGN PATENT DOCUMENTS 2078712   3/1993   Canada .

OTHER PUBLICATIONS

Heyman S, et al. (1992) "Mechanism of glycine protection in hypoxic injury: Analogies with glycine receptor," Kidney International, vol. 42, pp. 41–45.

*Primary Examiner*—Nathan M. Nutter

[57] ABSTRACT

Composition comprising glycine and/or other amino acids are useful in treating or minimizing the effects of endotoxemia, hypoxia-reperfusion injury and infection.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 7, 8 and 12–14 is confirmed.

Claims 1–6 and 9–11 are cancelled.

* * * * *